(12) United States Patent
Plazarte et al.

(10) Patent No.: US 11,744,730 B2
(45) Date of Patent: Sep. 5, 2023

(54) CORDLESS HEATING PAD

(71) Applicant: Sunbeam Products, Inc., Boca Raton, FL (US)

(72) Inventors: Enrique Plazarte, Fort Lauderdale, FL (US); Sergiu Mihail Pop, Lake Worth, FL (US)

(73) Assignee: Sunbeam Products, Inc., Atlanta, GA (US)

( * ) Notice: Subject to any disclaimer, the term of this patent is extended or adjusted under 35 U.S.C. 154(b) by 241 days.

(21) Appl. No.: 16/423,826

(22) Filed: May 28, 2019

(65) Prior Publication Data

US 2020/0375791 A1    Dec. 3, 2020

(51) Int. Cl.
*B32B 3/06* (2006.01)
*B32B 3/24* (2006.01)
(Continued)

(52) U.S. Cl.
CPC ............... *A61F 7/007* (2013.01); *A61F 7/02* (2013.01); *A61F 7/08* (2013.01); *B32B 5/02* (2013.01); *B32B 5/028* (2013.01); *B32B 5/26* (2013.01); *B32B 5/262* (2021.05); *B32B 5/265* (2021.05); *B32B 5/266* (2021.05); *B32B 5/275* (2021.05); *B32B 5/277* (2021.05); *B32B 5/279* (2021.05); *B32B 7/027* (2019.01); *B32B 7/09* (2019.01); *B32B 27/12* (2013.01); *B32B 27/36* (2013.01);
(Continued)

(58) Field of Classification Search
None
See application file for complete search history.

(56) References Cited

U.S. PATENT DOCUMENTS 1,594,053 A * 7/1926 Evans .................... H05B 3/342
                                                                34/95
2,339,409 A * 1/1944 Joy ........................ H05B 3/342
                                                                219/535
(Continued)

FOREIGN PATENT DOCUMENTS

CN       101961181 A *  2/2011    ......... A41D 13/0051
CS          269153 B1 *  4/1990
(Continued)

OTHER PUBLICATIONS

Machine Translation of JP-07192851-A, Jul. 1995 (Year: 1995).*
(Continued)

*Primary Examiner* — Jeffrey A Vonch
(74) *Attorney, Agent, or Firm* — Husch Blackwell LLP

(57) ABSTRACT

A heating pad includes a heat pad with an anterior and posterior side. The heat pad includes a first layer, a second layer, and a third layer. The second layer is located in between the first layer and the third layer. The first layer is located on the posterior side, while the third layer is located on the anterior side. The second layer has a wire selectively heated to increase the temperature of the heat pad. The third layer is a reflective material positioned to reflect heat from the second layer towards the first layer, decreasing heat emitted on the anterior side of the heat pad. The heating pad also includes a battery storage section for securing a battery. The battery is in electronical communication with the wire of the heat pad. The heating pad further includes an engagement mechanism to secure the heating pad to a user.

15 Claims, 10 Drawing Sheets

(51) Int. Cl.
  *B32B 5/02* (2006.01)
  *B32B 5/26* (2006.01)
  *A61F 7/00* (2006.01)
  *A61F 7/08* (2006.01)
  *B32B 7/027* (2019.01)
  *A61F 7/02* (2006.01)
  *B32B 27/12* (2006.01)
  *B32B 27/36* (2006.01)
  *B32B 7/09* (2019.01)
  *H05B 3/34* (2006.01)
  *B32B 33/00* (2006.01)
  *H01M 10/48* (2006.01)
  *H01M 10/42* (2006.01)
  *B32B 3/30* (2006.01)
  *B32B 3/26* (2006.01)
  *B32B 7/04* (2019.01)
  *H05B 3/36* (2006.01)

(52) U.S. Cl.
  CPC . *A61F 2007/0001* (2013.01); *A61F 2007/008* (2013.01); *A61F 2007/0071* (2013.01); *A61F 2007/0078* (2013.01); *A61F 2007/0088* (2013.01); *A61F 2007/0095* (2013.01); *A61F 2007/025* (2013.01); *A61F 2007/0228* (2013.01); *A61F 2007/0231* (2013.01); *A61F 2007/0244* (2013.01); *A61F 2007/0253* (2013.01); *A61F 2007/0255* (2013.01); *B32B 3/06* (2013.01); *B32B 3/266* (2013.01); *B32B 3/30* (2013.01); *B32B 5/022* (2013.01); *B32B 5/024* (2013.01); *B32B 5/026* (2013.01); *B32B 7/04* (2013.01); *B32B 33/00* (2013.01); *B32B 2250/04* (2013.01); *B32B 2250/05* (2013.01); *B32B 2250/20* (2013.01); *B32B 2255/10* (2013.01); *B32B 2255/205* (2013.01); *B32B 2262/0261* (2013.01); *B32B 2262/0276* (2013.01); *B32B 2262/0284* (2013.01); *B32B 2262/16* (2021.05); *B32B 2307/30* (2013.01); *B32B 2307/302* (2013.01); *B32B 2307/304* (2013.01); *B32B 2307/416* (2013.01); *B32B 2367/00* (2013.01); *B32B 2535/00* (2013.01); *H01M 10/425* (2013.01); *H01M 10/488* (2013.01); *H05B 3/34* (2013.01); *H05B 3/342* (2013.01); *H05B 3/36* (2013.01); *H05B 2203/003* (2013.01); *H05B 2203/014* (2013.01); *H05B 2203/015* (2013.01); *Y10T 428/23907* (2015.04); *Y10T 428/24008* (2015.01); *Y10T 428/24033* (2015.01); *Y10T 428/24322* (2015.01); *Y10T 428/24331* (2015.01); *Y10T 428/24562* (2015.01); *Y10T 442/3195* (2015.04); *Y10T 442/3707* (2015.04); *Y10T 442/3732* (2015.04); *Y10T 442/45* (2015.04); *Y10T 442/60* (2015.04); *Y10T 442/656* (2015.04); *Y10T 442/659* (2015.04); *Y10T 442/671* (2015.04)

(56) References Cited

U.S. PATENT DOCUMENTS

| | | | | |
|---|---|---|---|---|
| 2,590,212 | A * | 3/1952 | Samuels | H05B 3/342 224/930 |
| 2,617,916 | A * | 11/1952 | Neidnig | H05B 3/342 219/535 |
| 2,735,926 | A * | 2/1956 | Langlois | H05B 3/342 219/528 |
| 2,782,289 | A * | 2/1957 | Nathanson | H05B 3/16 219/217 |
| 2,948,802 | A * | 8/1960 | Shaw | H05B 3/342 219/212 |
| 3,084,241 | A * | 4/1963 | Carrona | H05B 3/342 2/81 |
| 3,407,818 | A * | 10/1968 | Costanzo | A61F 7/007 219/535 |
| 3,500,014 | A * | 3/1970 | Santo | H05B 3/342 219/512 |
| 3,501,616 | A * | 3/1970 | Stanley | H05B 3/342 2/93 |
| 3,524,965 | A * | 8/1970 | Stanley | H05B 3/342 219/528 |
| 3,748,436 | A * | 7/1973 | Cossaboom | H05B 3/342 607/108 |
| 4,310,745 | A * | 1/1982 | Bender | H05B 3/34 392/435 |
| 4,736,088 | A * | 4/1988 | Bart | A61F 7/007 219/211 |
| 4,798,936 | A * | 1/1989 | Johnson, Sr. | A47C 21/048 219/212 |
| 5,008,517 | A * | 4/1991 | Brekkestran | H05B 3/342 219/549 |
| 5,371,340 | A * | 12/1994 | Stanfield | A01K 1/0158 219/217 |
| 5,737,774 | A * | 4/1998 | Petty-Saphon | A61F 7/02 2/44 |
| 5,893,991 | A * | 4/1999 | Newell | H05B 3/342 219/211 |
| 5,970,718 | A * | 10/1999 | Arnold | A61F 7/10 607/109 |
| 6,664,512 | B2 * | 12/2003 | Horey | H05B 3/342 219/528 |
| 8,133,264 | B1 * | 3/2012 | LaFontaine | A61F 7/007 607/112 |
| 2002/0086599 | A1 * | 7/2002 | McNally | D04H 3/10 442/117 |
| 2005/0082280 | A1 * | 4/2005 | Ferguson | A61F 7/007 219/528 |
| 2006/0006168 | A1 * | 1/2006 | Rock | H05B 3/342 219/545 |
| 2006/0224221 | A1 * | 10/2006 | Purcell | A61F 7/034 607/114 |
| 2007/0016271 | A1 * | 1/2007 | Hammond | A61F 7/007 607/96 |
| 2007/0164010 | A1 * | 7/2007 | Rock | A41D 31/065 219/212 |
| 2008/0047955 | A1 * | 2/2008 | Rock | H05B 3/342 219/545 |
| 2008/0077212 | A1 * | 3/2008 | Hammac | A61F 7/007 607/108 |
| 2008/0083721 | A1 * | 4/2008 | Kaiserman | H05B 3/342 219/211 |
| 2008/0083740 | A1 * | 4/2008 | Kaiserman | A43B 3/35 219/520 |
| 2008/0188911 | A1 * | 8/2008 | Chao | A61N 1/326 607/96 |
| 2009/0025127 | A1 * | 1/2009 | McFie | A41D 23/00 2/455 |
| 2009/0107984 | A1 * | 4/2009 | Kohn | A61F 7/007 219/528 |
| 2011/0220634 | A1 * | 9/2011 | Yeh | A43B 3/34 219/482 |
| 2012/0055918 | A1 * | 3/2012 | Yue | H05B 3/34 219/552 |
| 2012/0191164 | A1 * | 7/2012 | Gander | H05B 3/12 219/528 |
| 2012/0222192 | A1 * | 9/2012 | Carey | A61F 7/02 2/171.2 |
| 2012/0240918 | A1 * | 9/2012 | Kirsch | A61F 7/02 126/263.01 |
| 2013/0270882 | A1 * | 10/2013 | Mills | B62B 5/0013 297/219.12 |
| 2014/0356574 | A1 * | 12/2014 | Conolly | B32B 5/24 428/138 |
| 2015/0134034 | A1 | 5/2015 | Terrell | |

(56) References Cited

U.S. PATENT DOCUMENTS

| | | | | |
|---|---|---|---|---|
| 2016/0374411 A1* | 12/2016 | Brooks | ............ | A61F 7/007 |
| | | | | 165/104.21 |
| 2017/0056644 A1* | 3/2017 | Chahine | ............ | A61N 1/36014 |
| 2018/0193185 A1* | 7/2018 | Thomas | ............ | A61F 7/02 |
| 2018/0280190 A1* | 10/2018 | Betkowski | ........ | A41D 13/0051 |
| 2019/0009105 A1* | 1/2019 | Sheng | ............ | A61F 7/007 |
| 2019/0029877 A1* | 1/2019 | Betkowski | ............ | A41D 27/205 |
| 2019/0060106 A1* | 2/2019 | Zabel | ............ | A61F 7/0085 |
| 2019/0269180 A1* | 9/2019 | Desmeules | ......... | A41D 19/001 |
| 2020/0008973 A1* | 1/2020 | Dunbar | ............ | A61F 7/00 |
| 2020/0138625 A1* | 5/2020 | Hope | ............ | A61F 7/034 |
| 2020/0214369 A1* | 7/2020 | Winningham | ......... | A41D 13/08 |
| 2020/0281046 A1* | 9/2020 | Beuckelaere | ............ | A61F 7/10 |

FOREIGN PATENT DOCUMENTS

| | | | | | |
|---|---|---|---|---|---|
| DE | 3112676 | A | * | 6/1982 | ............ A61F 7/00 |
| DE | 102008058744 | A1 | * | 5/2010 | ........ A41D 13/0051 |
| EP | 677283 | A1 | * | 10/1995 | ............ A61B 6/045 |
| EP | 0854696 | A1 | | 7/1998 | |
| GB | 2261822 | A | * | 6/1993 | ............ A61F 7/02 |
| GB | 2457486 | A | * | 8/2009 | ........ A41D 13/0051 |
| JP | 07192851 | A | * | 7/1995 | |
| JP | 2009009835 | A | * | 1/2009 | |
| KR | 200264050 | Y1 | * | 2/2002 | ............ A61F 7/007 |
| KR | 2003080953 | A | * | 10/2003 | ............ A61F 7/007 |
| KR | 2007095630 | A | * | 10/2007 | ........ A41D 13/0051 |
| KR | 1227227 | B1 | * | 1/2013 | ............ A61F 7/007 |
| KR | 20140120657 | A | * | 10/2014 | |
| KR | 2015040177 | A | * | 4/2015 | ............ A61F 7/007 |
| KR | 1537921 | B1 | * | 7/2015 | ............ A61F 7/007 |
| KR | 101684794 | B1 | * | 12/2016 | |
| KR | 101731248 | B1 | * | 5/2017 | |
| KR | 2018022146 | A | * | 3/2018 | ............ A61F 13/02 |
| KR | 1860750 | B1 | * | 6/2018 | .......... A61F 13/148 |
| KR | 200487879 | Y1 | * | 11/2018 | |
| KR | 2020190000410 | U | | 2/2019 | |
| RU | 2236942 | C2 | * | 9/2004 | |
| WO | WO-9962302 | A1 | * | 12/1999 | ............ A61F 7/007 |
| WO | WO-03059099 | A1 | * | 7/2003 | ........ A41D 13/0051 |
| WO | WO-2005122807 | A1 | * | 12/2005 | ........ A41D 13/0051 |
| WO | WO-2011157394 | A1 | * | 12/2011 | ............ A61F 7/007 |

OTHER PUBLICATIONS

Machine Translation of JP-2009009835-A, Jan. 2009 (Year: 2009).*
Machine Translation of KR-20140120657-A, Oct. 2014 (Year: 2014).*
Machine Translation of KR-101684794-B1, Dec. 2016 (Year: 2016).*
Machine Translation of KR-101731248-B1, May 2017 (Year: 2017).*
EcoLadyUK, Menstrual Pad Fabrics Comparison, Sep. 2013 (Year: 2013).*
Machine Translation o fKR-200487879-Y1, Nov. 2018 (Year: 2018).*
Machine Translation of CS-269153-B1, Apr. 1990 (Year: 1990).*
Machine Translation of RU-2236942-C2, Sep. 2004 (Year: 2004).*
Marshall, What Are the Warmest Materials for Winter?, Dec. 2012, <https://www.ehow.com/info_8507464_warmest-materials-winter.html> (Year: 2012).*

* cited by examiner

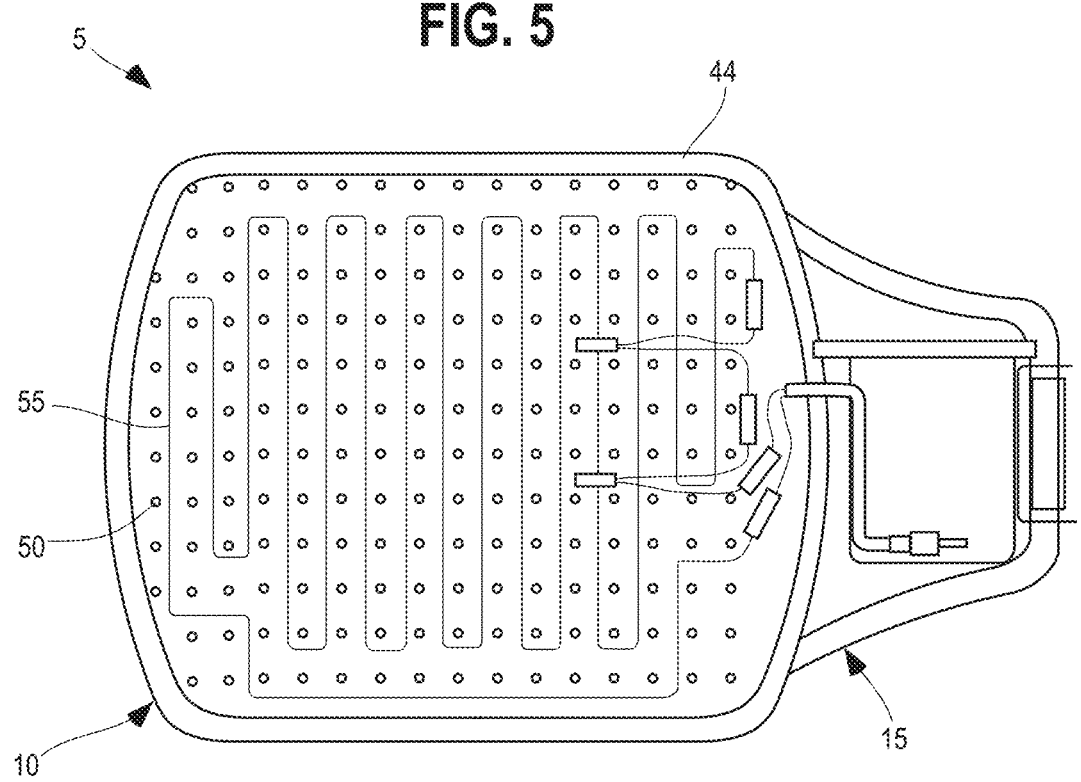

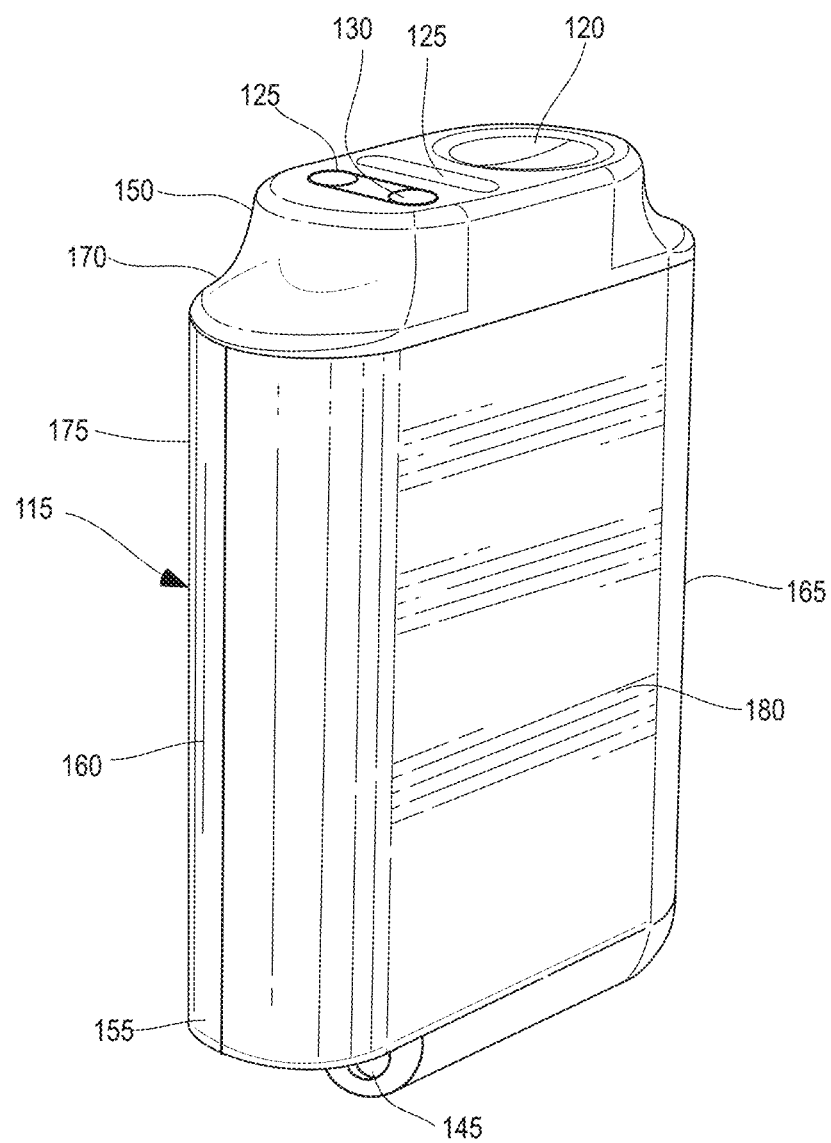

CORDLESS HEATING PAD

FIELD OF INVENTION

The invention refers to heating pads. More specifically, the invention includes heating pads that use a battery as a power source.

BACKGROUND OF THE INVENTION

Clinical studies have shown that the application of heat can provide relief for muscle and joint pain. Chronic pain sufferers are open to using non-oral pain relief methods, such as heat pads. Current heating pads require a large amount of power to provide a high-level of heat due to heat lost to the ambient air. Therefore, current heating pads are plugged into an outlet to provide the necessary high-level of heat. These heating pads can only be used at home when the user has at least 30 minutes.

Despite the convenience offered by battery-powered heating pads compared to corded heating pads, battery powered heating pads have not been successful in the market. Battery powered heating pads either require a large and unwieldy battery to provide sufficient power for a high-level of heat or the battery runs out of power too quickly. Large batteries are heavy and uncomfortable to wear, reducing the likelihood that consumers will buy and use the heating pad. A heating pad that runs out of power too quickly also reduces the likelihood that consumers will buy and use the heating pad because they would not receive the benefits of the heating pad if it runs out of power. It is therefore desirable for a portable heating pad that delivers a high-level of heat, while still being comfortable to wear.

SUMMARY OF THE INVENTION

A heating pad comprising a heat pad, a battery storage section, a battery, and an engagement mechanism. The heat pad has an anterior side and a posterior side, where the posterior side is adjacent to and faces the user and the anterior side of the heat pad faces away from the user when the heating pad is worn. The heat pad may include a series of flexible layers, allowing it to conform to the part of the user's body. In one embodiment, the series of layers include a micromink layer that extends over the posterior side of the heat pad. Adjacent to the micromink layer, the heat pad may include a nylon layer. A wire may attach to the nylon layer. The heat pad also includes a reflective layer that can reflect heat radiated towards the anterior side back towards the posterior side of the heat pad so that less heat is lost to the ambient air. The reflective layer may have an air gap on both sides. Finally, the heat pad may further include a polyester batting fiber layer and a brushed polyester layer. The micromink layer and the brushed polyester layer are the visible outer layers of the heating pad on the posterior and anterior sides, respectively.

The battery storage section includes a pocket member shaped and sized so that the battery pack may be inserted and secured within the pocket member. The pocket member includes an aperture that allows a cord to extend from the wire inside the heat pad to the pocket member, where the cord may be plugged into the battery pack. The battery pack can therefore serve as the power source for the heating pad. The battery pack may include at least one indicator and a button, where the indicator may show the amount of power within the battery pack and whether it is charging. The button may be used to turn on and off the heating pad, as well as to adjust the temperature. The battery pack also includes a charging port where a plug may be inserted into the charging port to charge the battery pack.

In order to use the heating pad, the user may place the heating pad onto the desired part of the body and wrap the engagement mechanism around the area to secure the heating pad in place. In one embodiment, the engagement mechanism is a strap that may engage the heating pad through a hook and loop engagement.

BRIEF DESCRIPTION OF THE DRAWINGS

For a better understanding of the various embodiments of the present invention, reference may be made to the accompanying drawings in which:

FIG. 5 is a cross sectional view of the heat pad of FIG. 2 taken at line 2-2;

FIG. 9 is a top perspective view of a battery pack;

Figure 1:
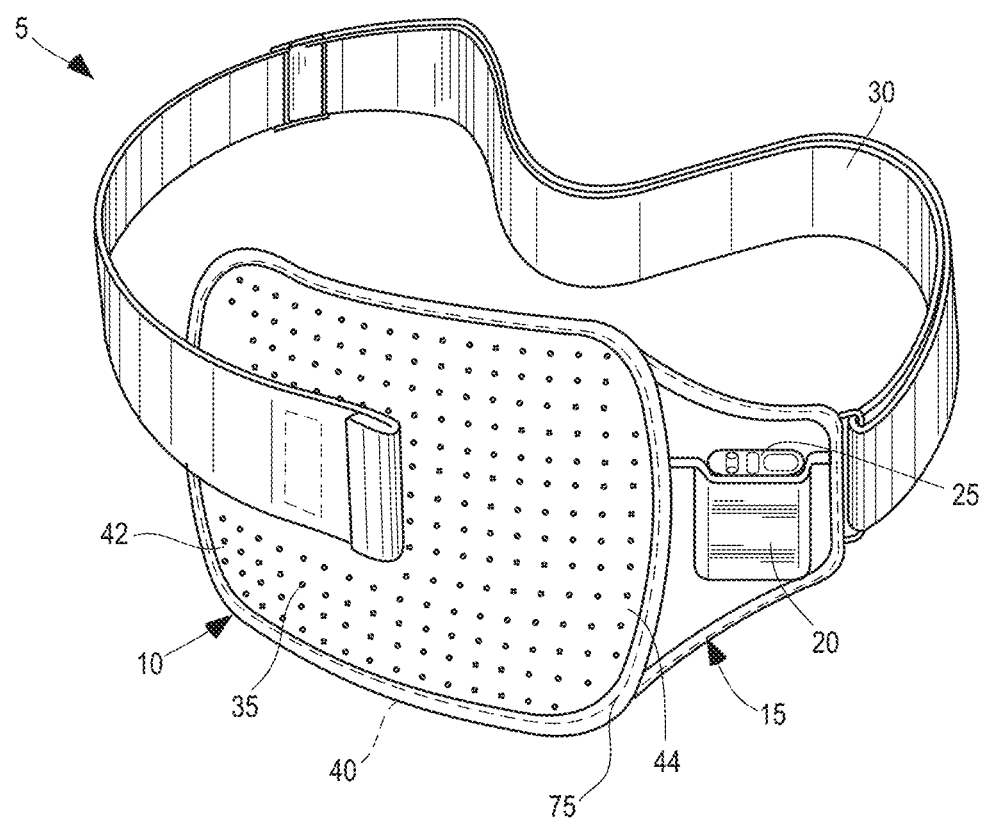
FIG. 1 is a front perspective view of a heating pad.

While the disclosure is susceptible to various modifications and alternative forms, specific embodiments thereof are shown by way of example in the drawings and will herein be described in detail. It should be understood, however, that the drawings and detailed description presented herein are not intended to limit the disclosure to the particular embodiment disclosed, but on the contrary, the intention is to cover all modifications, equivalents, and alternatives falling within the spirit and scope of the present disclosure.

DETAILED DESCRIPTION OF THE DRAWINGS

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

As illustrated in FIG. 1, the heating pad 5 includes a heat pad 10, a battery storage section 15, a pocket member 20, a battery pack 25, and an engagement mechanism 30. The heating pad 5 includes an anterior side 35 and a posterior side 40. The anterior side 35 of the heating pad 5 faces outwardly from a wearer and is visible when the heating pad 5 is worn. The posterior side 40 of the heating pad 5 is the side adjacent to the wearer when the heating pad 5 is worn.

The heating pad 5 also includes the engagement mechanism 30. In one embodiment, the engagement mechanism 30 is a strap adjacent to the battery storage section 15, on the opposite side from the heat pad 10. Thus, the heating pad 5 can include the heat pad 10, battery storage section 15, and the engagement mechanism 30. The engagement mechanism 30 may include a hook, while the anterior side 35 of heat pad 10 is preferably made out of material that may selectively engage the hooks on the engagement mechanism 30 in a hook and loop engagement. For example, the material may be brushed polyester or 3D spacer mesh fabric. The material on the anterior side 35 of the heat pad 10 allows the engagement mechanism 30 to selectively engage the heat pad 10 through a hook and loop engagement. In alternative embodiments, the engagement mechanism 30 may be other types of engagement mechanism other than a hook and loop.

Figure 2:
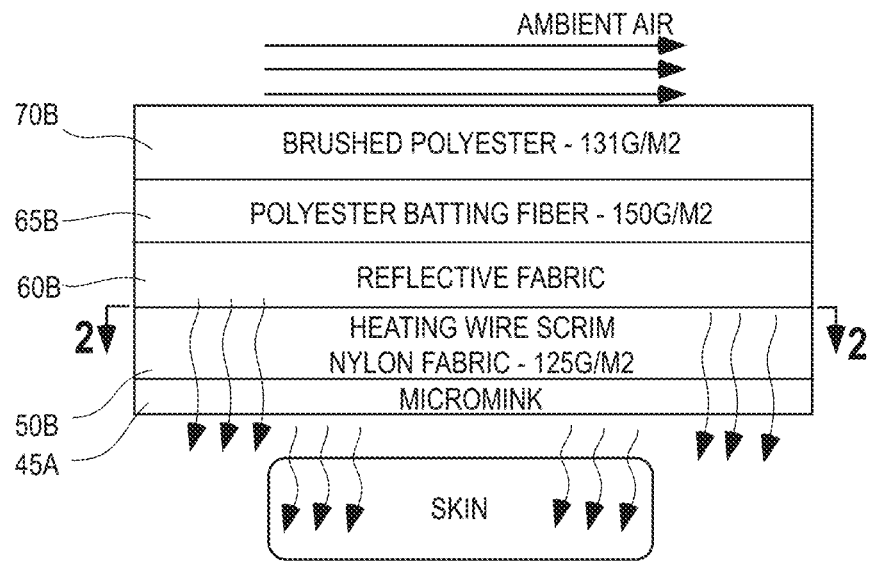
FIG. 2 is a flow chart of the layers in a first embodiment of a heat pad.

In an example embodiment, the heat pad 10 may be a planar rectangular member with a first heating pad end 42 and a second heating pad end 44. The heat pad 10 preferably includes at least three flexible layers, allowing it to conform to the part of the user's body that the heating pad 5 is placed onto. In a first embodiment and as shown in FIG. 2, the series of layers include a first layer 45A that covers the posterior side 40 of the heat pad 10A and is positioned adjacent to the user when the heating pad 5 is worn. The first layer 45A is the layer that comes into contact with the user's skin or clothing and preferably provides a comfortable surface that does not irritate the skin of the user when the heating pad 5 is worn and is also able to transfer heat. The first layer 45A may be a micromink layer. The heat pad 10A preferably further includes a second layer 50A which provides a surface for a wire (known hereinafter as wire 55 and shown in FIG. 5) to be attached to, as will be explained in more detail hereinafter. The second layer 50A may be a nylon layer. The nylon fabric may have a weight of 125 g/m2.

The heat pad 10A also includes a third layer 60A. The second layer 50A is therefore located and positioned in between the first layer 45A and the third layer 60A. The third layer 60A can be any type of fabric or material that can reflect heat towards the posterior side 40 of the heat pad 10 so that the posterior side 40 of the heat pad 10A is warmer than the anterior side 35 of the heat pad 10A. In one embodiment, the third layer 60A may comprise hollow, polyester fibers needle punched through both a nonwoven substrate and a reflective metalized polyester film. The third layer 60A may further be surrounded on both sides by an air gap or air space.

As shown, the heat pad 10 further includes a fourth layer 65A located and positioned on the anterior side 35 of the third layer 60A. The third layer 60A is therefore located and positioned in between the second layer 50A and the fourth layer 65A. The fourth layer 65A may be a polyester batting fiber layer. The polyester batting fiber layer may have a weight of 150 g/m2. Finally, the heat pad 10A includes a fifth layer 70A, which may be a brushed polyester layer in one embodiment. The brushed polyester layer may have a weight of 131 g/m2. The visible outer layers of the heating pad 5 include the first layer 45A and the fifth layer 70A, where only the fifth layer 70A is visible when the heating pad 5 is worn.

A bias tape 75 (shown in FIG. 1) may cover the raw edge or perimeter of the first layer 45A, the second layer 50A, the third layer 60A, the fourth layer 65A, and the fifth layer 70A by enveloping the perimeters of the series of layers. The bias tape 75 may be secured around the perimeter of the series of layers by sewing, gluing, or any other method known in the art, thereby preferably preventing the perimeters of the series of layers from causing discomfort to the wearer.

Figure 3:
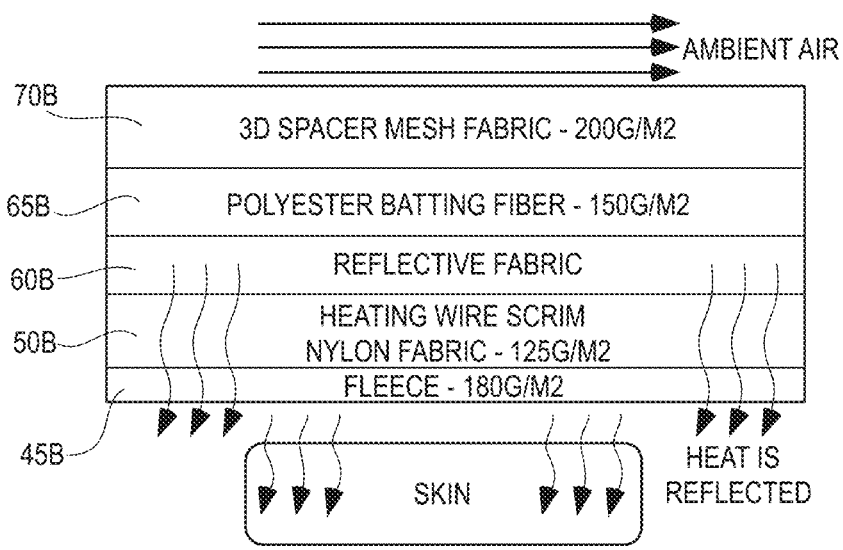
FIG. 3 is a flow chart of the layers in a second embodiment of the heat pad.

As shown in FIG. 3, in a second embodiment of the heat pad 10B, the series of layers of the heat pad 10B may differ. As in the first embodiment, the layers of the heat pad 10B are also preferably flexible, rectangular, and the same or similar in size. The posterior side 40 of the heat pad 10 may be covered by a first layer 45B so that the first layer 45B is adjacent to the user when the heating pad 5 is worn. In a one embodiment, the first layer 45B may be a fleece layer. The fleece fabric may have a weight of 180 g/m2. Similarly to the first layer 45A of the first embodiment, the first layer 45B of the second embodiment provides a comfortable surface and also allows for the transfer of heat.

As in the first embodiment, the second embodiment of the heat pad 10B may further include the second layer 50B and the third layer 60B as discussed in connection with the previous embodiment. The second layer 50B and the third layer 60B may be a nylon layer (125 g/m2) and a reflective fabric layer, respectively. The second layer 50B also has a wire (also known as wire 55 hereinafter) that may be attached to its surface or run through the second layer 50B.

The second layer 50B is therefore in between the first layer 45B and the third layer 60B. The third layer 60B can further be adjacent to the fourth layer 65B. The fourth layer 65B may be a polyester batting fabric layer. The polyester batting fabric layer may be 150 g/m2. As in the first embodiment, the third layer 60B reflects heat back towards the user so that less heat is lost to the ambient air. Similarly, the third layer 60B may also have an air gap between the second layer 50B and third layer 60B, as well as between the third layer 60B and fourth layer 65B. The fourth layer 65B may also be located and positioned in between the third layer 60 and the fifth layer 70. In the second embodiment, the fifth layer 70 may be a 3D spacer mesh fabric. The 3D spacer mesh fabric may have a weight of 200 g/m2. The second embodiment of the heat pad 10B therefore includes the first layer 45B, second layer 50B, third layer 60B, fourth layer 65B, and fifth layer 70B, where only the first layer 45B and the fifth layer 70B are visible. Only the fifth layer 70B can be seen when the heating pad 5 is worn. The bias tape 75 (shown in FIG. 1) may also surround the raw edge or perimeter the first layer 45B, second layer 50B, third layer 60B, fourth layer 65B, and fifth layer 70B.

Figure 4:
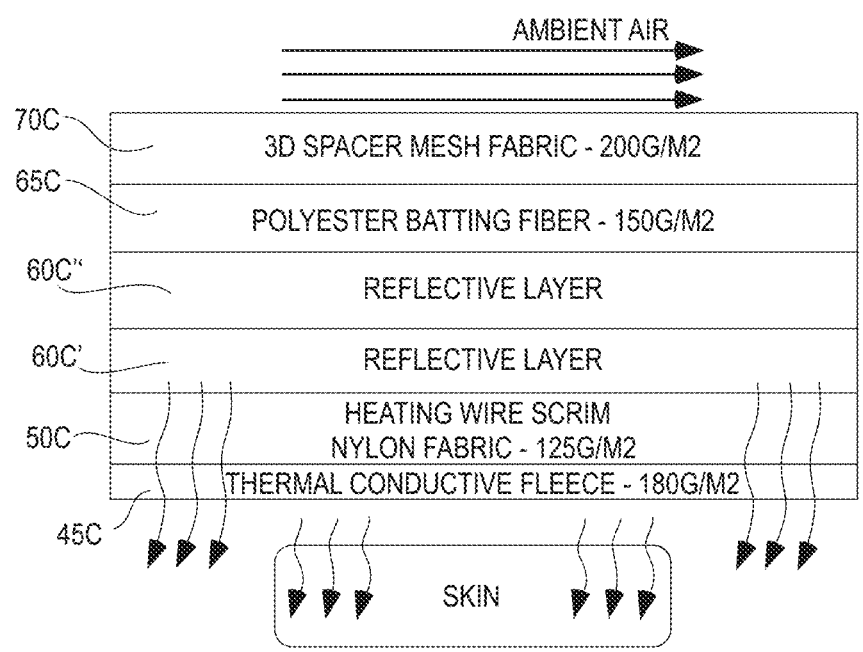
FIG. 4 is a flow chart of the layers in a third embodiment of the heat pad.

FIG. 4 illustrates a third embodiment of a heat pad 10C. The third embodiment may be substantially similar to the second embodiment. However, the third embodiment can include two third layers 60C' and 60C", instead of just a single third layer 60 as in the first and second embodiments. There may also be an air gap in between the second layer 50C and third layer 60C', third layer 60C' and third layer 60C", and third layer 60C" and fourth layer 65C. The third embodiment may therefore include the first layer 45C, second layer 50C, third layer 60C', third layer 60C", fourth layer 65C, and fifth layer 85C, where the layers are made out of thermal conductive fleece (180 g/m2), nylon (125 g/m2), reflective fabric, reflective fabric, polyester batting fabric (150 g/m2), and 3D spacer mesh (200 g/m2), respectively. The third embodiment may also include the bias tape 75 (illustrated in FIG. 1) that surrounds and wraps around the raw edges or perimeter of the layers of the heat pad 10C.

Thus, in the example embodiments above, the first layer 45 may be micro mink or a fleece layer. The second layer 50 may be nylon, while the third layer 60 is a fabric that may reflect heat. The third layer 60 may include one or two layers of the reflective fabric, and may also include an air space in between the layers. The fourth layer 65 may be polyester batting fiber. Finally, the fifth layer 70 may be a brushed polyester or a mesh fabric. While the example embodiments of the heat pad 10 include at least five layers, the heat pad 10 may only include the first layer 45, the second layer 50 (with a wire attached), and the third layer 60.

In each of the embodiments of the heat pad 10, the wire 55 is attached to the second layer 50 and extends substantially over the entirety of the heat pad 10, as shown in FIG. 5. In other embodiments, the pattern of wire 55 attachments may differ than what is shown in the FIG. 5. Alternatively, the wire 55 may run through the second layer 50. The wire 55 is connected to the battery pack 25 through a cord 105, as will be explained in more detail hereinafter. The battery pack 25 provides power to run electricity through the wire 55 which heats the heat pad 10. Thus, the second layer 50 may be the heating layer. In one embodiment, the wire 55 may be a low voltage DC wire. However, the wire 55 may be other types of wires in alternative embodiments.

Figure 6A:
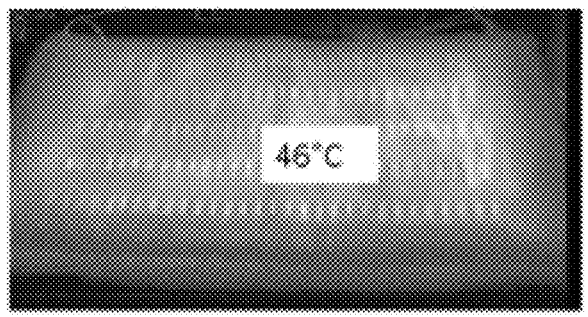
FIG. 6A is an anterior side of the prior art heat pad.
Figure 6B:
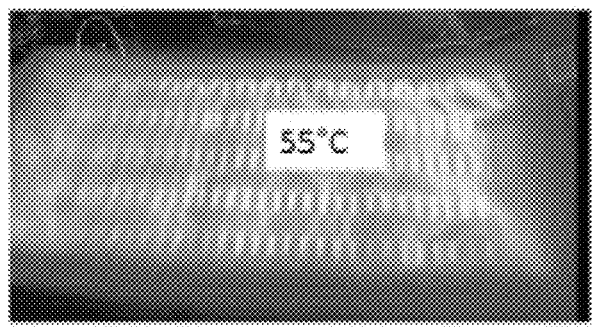
FIG. 6B is a posterior side of the prior art heat pad of FIG. 6A.
Figure 6C:
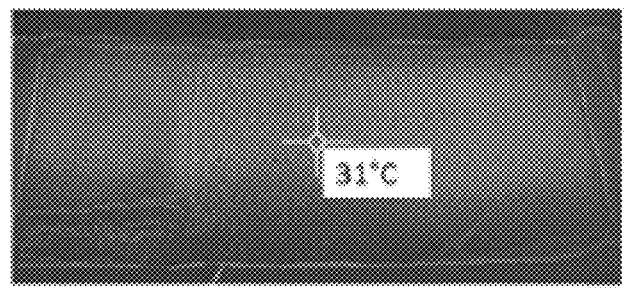
FIG. 6C is an anterior side of the first embodiment of the heat pad of FIG. 2.
Figure 6D:
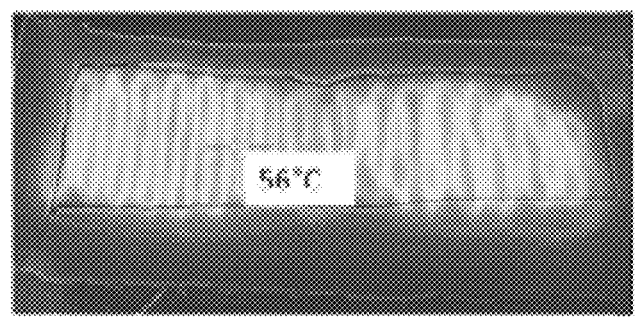
FIG. 6D is a posterior side of the first embodiment of the heat pad of FIGS. 2 and 6C.

The third layer 60, a reflective layer in all three embodiments of the heat pad 10, reduces the amount of heat that radiates from the anterior side 35 of the heat pad 10 and is lost to the ambient air. As seen in FIGS. 6A and 6C, the exposed side or anterior side 35 of the heat pad 10 has a lower temperature than the anterior side of a prior art heating pad A. In greater detail and as illustrated in FIGS. 6A-6D, in a prior art heating pad A, the posterior side is 55° C., while its anterior side is 46° C. Similarly, the posterior side 40 of the heat pad 10 is 56° C. The anterior side 35 of the heat pad 10, however, is 31° C., 15 degrees cooler than the anterior side of the prior art heating pad A. The third layer 60 with its reflective fabric reduces the amount of heat lost to the ambient air, and preferably also reduces the amount of power necessary to produce a high-level of heat.

Figure 7:
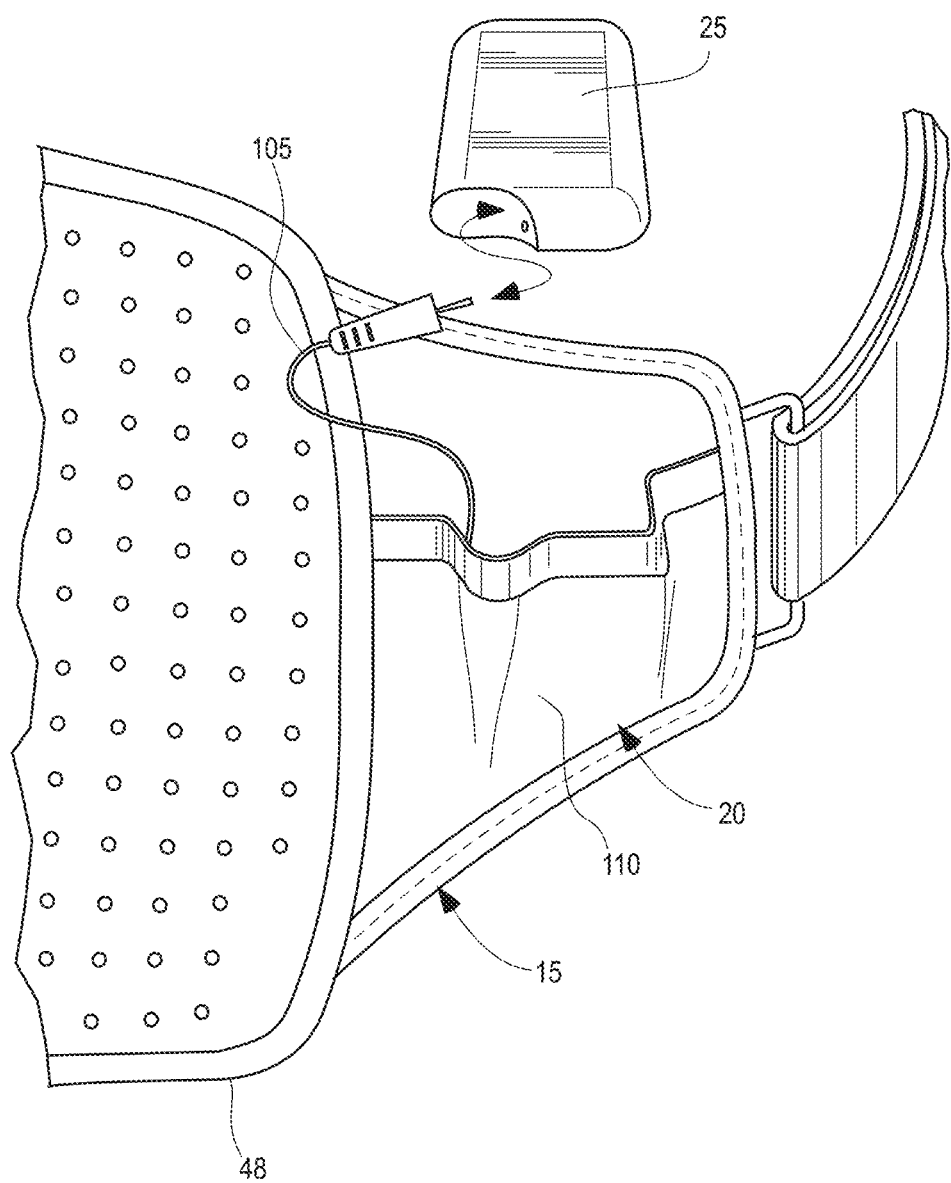
FIG. 7 is an enlarged front perspective view of a heating pad of FIG. 1.

In addition to the heat pad 10, the heating pad 5 also includes the battery storage section 15. In one embodiment, the battery storage section 15 is located and positioned at the second heating pad end 44, illustrated in FIG. 7. The battery storage section 15 may be a quadrilateral that tapers inwardly as extends away from the heat pad 10. In other embodiments, the battery storage section 15 may be located and positioned in another area, as well as being a different shape and size.

The battery storage section 15 includes the pocket member 20. The pocket member 20 may serve as a receptacle for the battery pack 25, wherein the battery pack 25 is preferably placed and secured between the battery storage section 15 and a pocket layer 110. In one embodiment, the pocket member 20 may be formed by the pocket layer 110 located and positioned on the anterior side 35 of the battery storage section 15. The pocket member 20 may be attached to the battery storage section 15 by sewing, glue, or any other method known in the art. In yet another embodiment, the pocket member 20 may be integrally formed with the battery storage section 15.

Figure 8A:
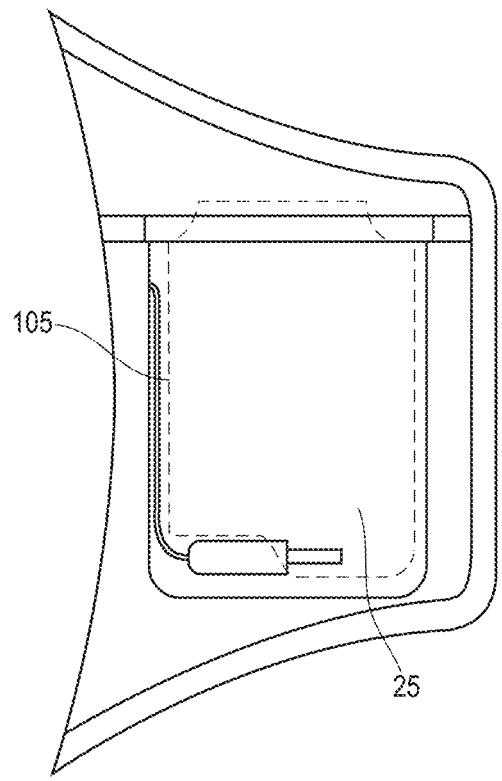
FIG. 8A is an elevation view of a pocket member and a cord.
Figure 8B:
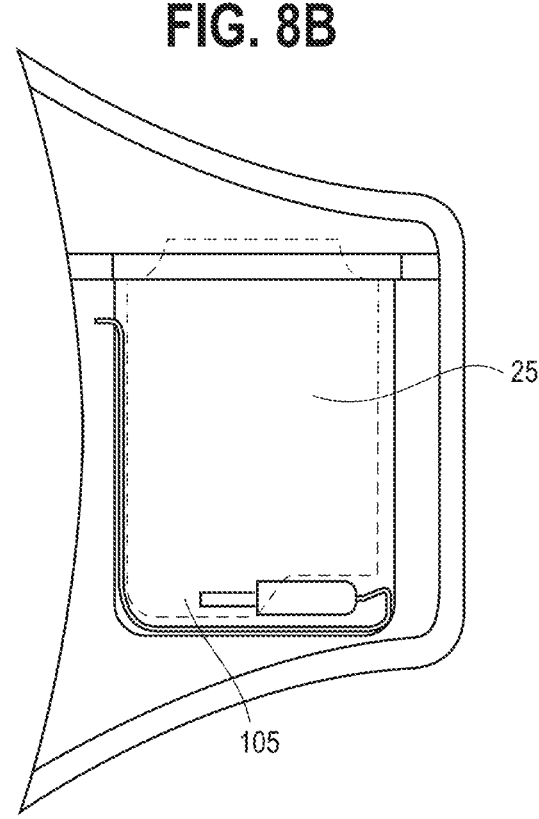
FIG. 8B is an elevation view of the pocket member and the cord of FIG. 8A.

The pocket member 20 preferably has an aperture (not shown) that connects the pocket member 20 to the heat pad 10. The heat pad 10 includes the cord 105 which extends from the heat pad 10 to the pocket member 20 through the aperture. The cord 105 can selectively engage with the battery pack 25. Turning to FIGS. 8A and 8B, the cord 105 is preferably long enough that the battery pack 25 may be inserted into the pocket member 20 with a heat pad port (known hereinafter as heat pad port 145) either facing the aperture or facing away from the aperture.

Figure 10:
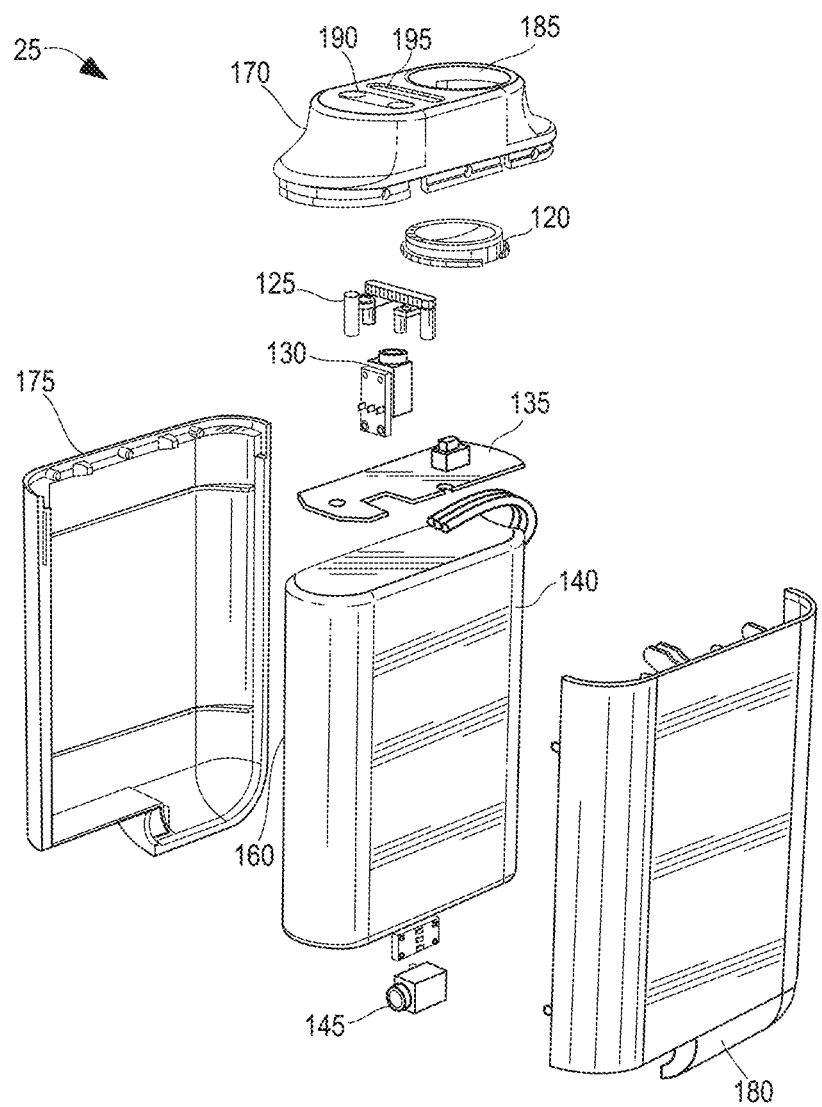
FIG. 10 is an exploded view of the battery pack of FIG. 9.

Turning to FIGS. 9 and 10, in one embodiment, the battery pack 25 may be a rectangular member. The battery pack 25 includes a housing 115, a button 120, at least one indicator 125, a charging port 130, a printed circuit board 135, a battery 140, and a heat pad port 145. The housing 115 surrounds the various components and parts of the battery pack 25. The housing 115 has a top housing end 150 and a bottom housing end 155. The housing 115 further includes a first housing end 160 and a second housing end 165. The housing 115 includes a top cover 170, a first side cover 175, and a second side cover 180. The first side cover 175 is preferably a rectangular member that curves inwards at the bottom housing end 155, the first housing end 160, and the second housing end 165. The second side cover 180 is preferably a mirror image of the first side cover 175. The first side cover 175 and second side cover 180 can preferably snap together to form the bottom and sides of the housing 115. The top cover 170 preferably is an oval-like shape that extends inwards and upwards at both the first housing end 160 and the second housing end 165. When the first side cover 175 and second side cover 180 are engaged with one another, the top cover 170 also preferably snaps into the aperture (not shown) created by the first and second side cover 175 and 180 to form the housing 115.

The housing 115 includes a series of apertures including a button aperture 185 and at least one indicator aperture 190. The button 120 extends through the button aperture 185, while the at least one indicator 125 extends through the at least one indicator aperture 190. The at least button aperture 185 allows the user to access and actuate the button 120. The button 120 may be actuated to adjust the temperature of the heat pad 10. The at least one indicator 125 may indicate the amount of power left in the battery 140 or if the battery 140 is charging. The battery 140 may be lithium ion battery, although other types of battery are also envisioned herein.

Figure 11:
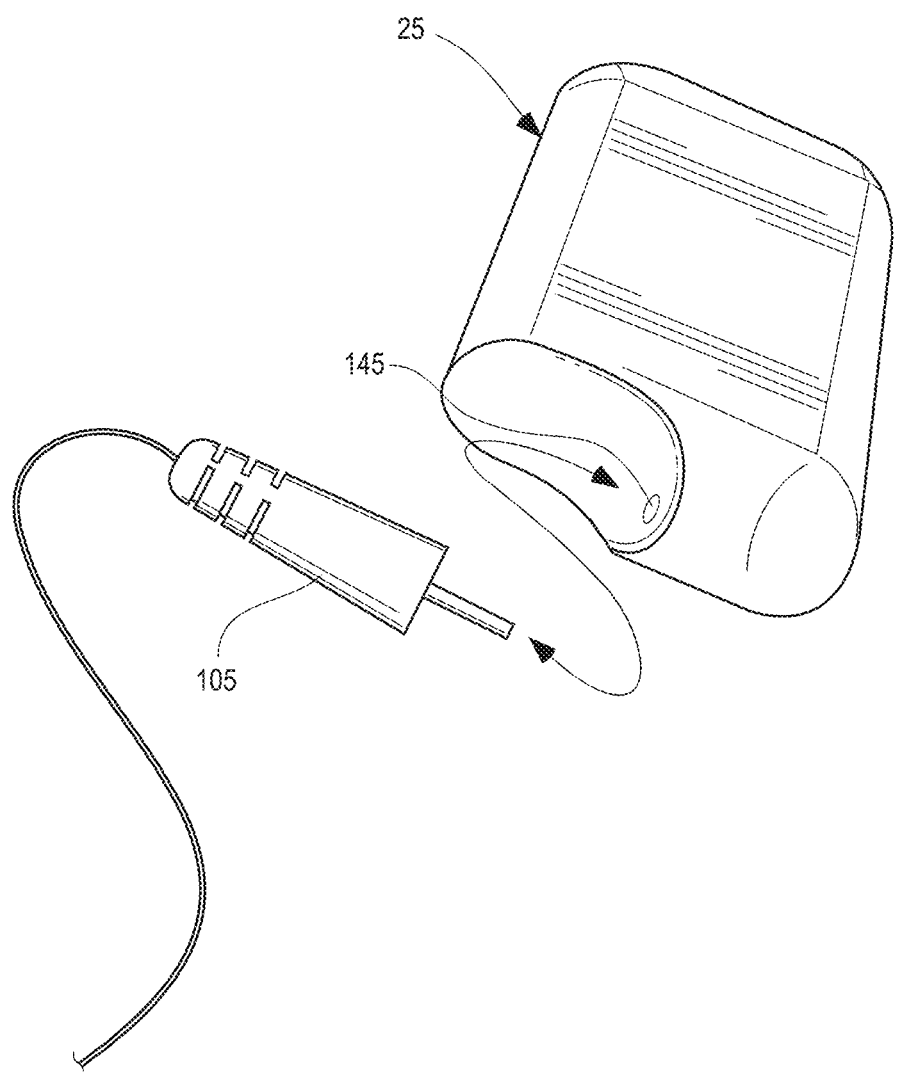
FIG. 11 is a bottom perspective view of the battery of FIGS. 9 and 10 and the cord of FIG. 8.

The housing 115 may further include a charging port aperture 195 and a heat pad port 145 so that a plug may be inserted into either the charging port 130 to charge the battery 140 or the heat pad port 145 (shown in FIG. 11) to heat the heat pad 10. The printed circuit board 135 may be mechanically and electrically connected to the battery 140, as well as the at least one indicator 125 and button 120.

Before using the heating pad 5, the user preferably charges the battery pack 25. In order to charge the battery pack 25, the user can insert a plug (not shown) into the charging port 130. The opposite end of the plug is preferably inserted into a wall socket so that the battery pack 25 is in mechanical and electrical connection with the wall socket. Once the battery pack 25 is charged, the battery pack 25 may be used as the power source for the heating pad 5. Once the battery 140 has been charged, the battery pack 25 may be disconnected from the plug. The cord 105 may then be inserted into the heat pad port 145 of the battery pack 25. Once the cord 105 has been inserted into the battery pack 25, the battery pack 25 may be placed within the pocket member 20. When a user desires to use the heating pad 5, the user may place the heating pad 5 onto the desired part of the body, wrap the engagement mechanism 30 around the area, and secure the heating pad 5 through a hook and loop engagement. The user may turn on the heating pad 5 and adjust the temperature through the button 120.

From the foregoing, it will be seen that the various embodiments of the present invention are well adapted to attain all the objectives and advantages hereinabove set forth together with still other advantages which are obvious and which are inherent to the present structures. It will be understood that certain features and sub-combinations of the present embodiments are of utility and may be employed without reference to other features and sub-combinations. Since many possible embodiments of the present invention may be made without departing from the spirit and scope of the present invention, it is also to be understood that all disclosures herein set forth or illustrated in the accompanying drawings are to be interpreted as illustrative only and not limiting. The various constructions described above and illustrated in the drawings are presented by way of example only and are not intended to limit the concepts, principles and scope of the present invention.

Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A heating pad comprising:
    a heat pad including an anterior side and a posterior side, the heat pad comprising:
        a first layer on the posterior side of the heat pad;
        a second layer having a wire, the wire capable of being selectively heated to increase the temperature of the heat pad;
        a third layer comprising a reflective fabric positioned to reflect heat from the second layer towards the first layer, thereby decreasing the amount of heat emitted on the anterior side of the heat pad, the reflective fabric comprising hollow polyester fibers passing through a reflective metallized film;
        the third layer being located further towards the anterior side than the first and second layers, the second layer being located in between the first layer and the third layer of the heat pad;
        a first air gap between the second layer and the third layer;
        a fourth layer comprising a batting fiber layer, the fourth layer being located further towards the anterior side than the third layer;
        a second air gap between the third layer and the fourth layer;
        a battery being in electronic communication with the wire of the heat pad; and
        an engagement mechanism to secure the heating pad to a user; and
        wherein the second and third layers are configured to direct heat generated in the second layer toward the posterior side and the first layer is configured to conduct the heat generated in the second layer to an outer surface of the posterior side.

2. The heating pad of claim 1, wherein the batting fiber layer is a polyester batting fiber layer.

3. The heating pad of claim 1, wherein the heat pad includes a fifth layer, the fifth layer comprising a brushed polyester layer or 3D spacer mesh fabric.

4. The heating pad of claim 1, wherein the first layer is a micro mink or fleece layer.

5. The heating pad of claim 1, wherein the second layer is a nylon layer.

6. The heating pad of claim 1, wherein the heating pad includes a battery storage section.

7. The heating pad of claim 1, wherein the battery pack includes a button for turning the heating pad on and off, as well as for adjusting the temperature.

8. The heating pad of claim 1, wherein the third layer comprises first and second sublayers of reflective fabric with a third air gap between the first and second sublayers of reflective fabric.

9. The heating pad of claim 1, wherein the engagement mechanism is a hook and loop engagement.

10. The heating pad of claim 1, wherein the battery pack includes a button and at least one indicator, the button being used for turning the heating pad on and off and adjusting the temperature of the heat pad, the at least one indicator being capable of indicating the power status of the battery pack.

11. The heating pad of claim 1, wherein the reflective metallized film comprises a reflective metallized polyester film.

12. The heating pad of claim 11, wherein the hollow polyester fibers pass through both the reflective metallized polyester film and a nonwoven substrate.

13. A heating pad comprising:
    a heat pad including an anterior side and a posterior side, the heat pad comprising:
        a first layer on the posterior side of the heat pad;
        a second layer having a wire, the wire capable of being selectively heated to increase the temperature of the heat pad;
        a third layer comprising a reflective fabric positioned to reflect heat from the second layer towards the first layer, thereby decreasing the amount of heat emitted on the anterior side of the heat pad, the reflective fabric comprising hollow polyester fibers passing through a reflective metallized film;
        the third layer being located further towards the anterior side than the first and second layers, the second layer being located between the first layer and the third layer of the heat pad;
        a first air gap between the second layer and the third layer;
        a fourth layer being located further towards the anterior side than the third layer;
        a second air gap between the third and the fourth layer;
        a fifth layer being located further towards the anterior side than the fourth layer, the fifth layer comprising a 3D spacer mesh fabric;
        a battery being in electronic communication with the wire of the heat pad; and
        an engagement mechanism to secure the heating pad to a user; and
        wherein the second and third layers are configured to direct heat generated in the second layer toward the posterior side and the first layer is configured to conduct the heat generated in the second layer toward the posterior side.

14. The heating pad of claim 13, wherein the fourth layer comprises a polyester batting fiber layer.

15. A heating pad comprising:
    a heat pad including an anterior side and a posterior side, the heat pad comprising:
        a first layer on the posterior side of the heat pad;
        a second layer having a wire, the wire capable of being selectively heated to increase the temperature of the heat pad;
        a third layer comprising a first sublayer of reflective fabric and a second sublayer of reflective fabric positioned to reflect heat from the second layer towards the first layer, thereby decreasing the amount of heat emitted on the anterior side of the heat pad, the reflective fabrics each comprising hollow polyester fibers passing through a reflective metallized film;

the third layer being located further towards the anterior side than the first and second layers, the second layer being located between the first layer and the third layer of the heat pad;

a first air gap between the second layer and the third layer;

a second air gap between the first sublayer of reflective fabric and the second sublayer of reflective fabric;

a fourth layer being located further towards the anterior side than the third layer;

a third air gap between the third layer and the fourth layer;

a battery being in electronic communication with the wire of the heat pad; and an engagement mechanism to secure the heating pad to a user; and wherein the second and third layers are configured to direct heat generated in the second layer toward the posterior side and the first layer is configured to conduct the heat generated in the second layer to an outer surface of the posterior side.

* * * * *